United States Patent
Gyrn et al.

(10) Patent No.: US 8,945,057 B2
(45) Date of Patent: Feb. 3, 2015

(54) CANNULA AND DELIVERY DEVICE

(75) Inventors: Steffen Gyrn, Ringsted (DK); Orla Mathiasen, Sorø (DK)

(73) Assignee: Unomedical A/S, Birkeroed (DK)

( * ) Notice: Subject to any disclaimer, the term of this patent is extended or adjusted under 35 U.S.C. 154(b) by 1652 days.

(21) Appl. No.: 12/375,849

(22) PCT Filed: Aug. 2, 2007

(86) PCT No.: PCT/DK2007/050103
§ 371 (c)(1), (2), (4) Date: Jul. 10, 2009

(87) PCT Pub. No.: WO2008/014791
PCT Pub. Date: Feb. 7, 2008

(65) Prior Publication Data
US 2010/0030155 A1 Feb. 4, 2010

(30) Foreign Application Priority Data
Aug. 2, 2006 (DK) .................. 2006 01027

(51) Int. Cl.
*A61M 5/178* (2006.01)
*A61M 5/142* (2006.01)
*A61M 5/158* (2006.01)
*A61M 25/06* (2006.01)
*A61M 5/32* (2006.01)
*A61M 25/00* (2006.01)
*A61M 25/02* (2006.01)

(52) U.S. Cl.
CPC ........... *A61M 5/14248* (2013.01); *A61M 5/158* (2013.01); *A61M 25/0612* (2013.01); *A61M 5/3243* (2013.01); *A61M 25/0097* (2013.01); *A61M 25/02* (2013.01); *A61M 2005/1581* (2013.01); *A61M 2005/1585* (2013.01); *A61M 2005/1587* (2013.01); *A61M 2205/12* (2013.01)
USPC .................................................... 604/164.08

(58) Field of Classification Search
USPC ................................ 604/164.01–164.08, 501
See application file for complete search history.

(56) References Cited

U.S. PATENT DOCUMENTS

| 1,592,462 A | 7/1926 | MacGregor |
| 2,047,010 A | 7/1936 | Dickinson |

(Continued)

FOREIGN PATENT DOCUMENTS

| DE | 4 432 329 A1 | 6/1994 |
| DE | 196 31 921 A1 | 3/1997 |

(Continued)

OTHER PUBLICATIONS

"Why inset®?" inset® infusion set product overview; http://web.archive.org/web/20040906102448/http://www.infusion-set.com/Default.asp?ID=108; two pages.

(Continued)

*Primary Examiner* — Manuel Mendez
(74) *Attorney, Agent, or Firm* — Lorelei Westin, Esq.

(57) ABSTRACT

The present application concerns a cannula device for mounting in a base part (9) comprising a housing (Ia, 16) and at least one membrane (4) together defining at least 15 one cavity, the cannula device further comprises a cannula (3) mounted in the housing and being in fluid communication with the at least one cavity, said cannula device is provided with means (5) for attaching the device to the base part (9) on the proximal side of the device.

24 Claims, 14 Drawing Sheets

(56) References Cited

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teissen-Simony |
| 5,527,287 A | 6/1996 | Miskinyar |

(56) References Cited

U.S. PATENT DOCUMENTS

| | | |
|---|---|---|
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| 6,387,076 B1 | 5/2002 | Van Lunduyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |

(56) References Cited

U.S. PATENT DOCUMENTS

| | | |
|---|---|---|
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 * | 4/2006 | Marano-Ford et al. ....... 604/157 |
| 7,047,070 B2 | 5/2006 | Wilkenson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 * | 7/2007 | Shermer et al. ............... 604/134 |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 * | 12/2001 | Marggi et al. ............ 604/164.11 |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Pluth et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 * | 11/2002 | Gray et al. .................... 604/506 |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 * | 9/2003 | Lynch et al. ................ 604/890.1 |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |

(56) References Cited

U.S. PATENT DOCUMENTS

| | | |
|---|---|---|
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1* | 2/2006 | Mogensen et al. ........ 604/164.01 |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1* | 6/2006 | Wojcik .......................... 604/506 |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1* | 11/2006 | Nielsen et al. ................. 604/174 |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheider et al. |
| 2007/0129691 A1 | 6/2007 | Sage, Jr. et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0058692 A1 | 3/2008 | Propp et al. |
| 2008/0200897 A1 | 8/2008 | Hoss et al. |
| 2008/0269687 A1 | 10/2008 | Chong |
| 2008/0312601 A1 | 12/2008 | Cane' |
| 2009/0062767 A1 | 3/2009 | Van Antwerp et al. |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1 | 9/2010 | Nielsen |
| 2010/0262078 A1 | 10/2010 | Blomquist |
| 2011/0054399 A1 | 3/2011 | Chong et al. |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0275230 A2 | 6/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 B1 | 12/1995 |
| EP | 0714631 B1 | 6/1996 |
| EP | 0744183 A2 | 11/1996 |
| EP | 0747006 A1 | 12/1996 |
| EP | 0799626 A1 | 10/1997 |
| EP | 0937475 A2 | 8/1999 |
| EP | 0 956 879 A1 | 11/1999 |
| EP | 1086718 A1 | 3/2001 |
| EP | 1125593 A1 | 8/2001 |
| EP | 0775501 B1 | 6/2002 |
| EP | 1329233 A1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |

(56) References Cited

FOREIGN PATENT DOCUMENTS

| | | |
|---|---|---|
| EP | 2272559 A1 | 1/2011 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| GB | 2 459 101 A | 10/2009 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/068014 A2 | 9/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/024219 A1 | 3/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A1 | 8/2007 |
| WO | WO 2007/122207 A1 | 11/2007 |
| WO | WO 2007/140631 A1 | 12/2007 |
| WO | WO 2007/140783 A1 | 12/2007 |
| WO | WO 2007/140785 A1 | 12/2007 |
| WO | WO 2007/141210 A1 | 12/2007 |
| WO | WO 2008/014792 A1 | 2/2008 |
| WO | WO 2008/033702 A1 | 3/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A1 | 8/2008 |
| WO | WO 2008/092959 A1 | 8/2008 |
| WO | WO 2008/135098 A1 | 11/2008 |
| WO | WO 2008/147600 A1 | 12/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/033032 A1 | 3/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/080715 A1 | 7/2010 |
| WO | WO 2010/112521 A1 | 10/2010 |
| WO | WO 2011/012465 A1 | 2/2011 |
| WO | WO 2011/015659 A1 | 2/2011 |

(56) References Cited

FOREIGN PATENT DOCUMENTS

| WO | WO 2011/121023 A1 | 10/2011 |
| WO | WO 2012/041784 A1 | 4/2012 |
| WO | WO 2012/041923 A2 | 4/2012 |
| WO | WO 2012/045667 A2 | 4/2012 |

OTHER PUBLICATIONS

International Preliminary Report on Patentability completed Nov. 4, 2008 for International Application No. PCT/DK2007/050103.

* cited by examiner

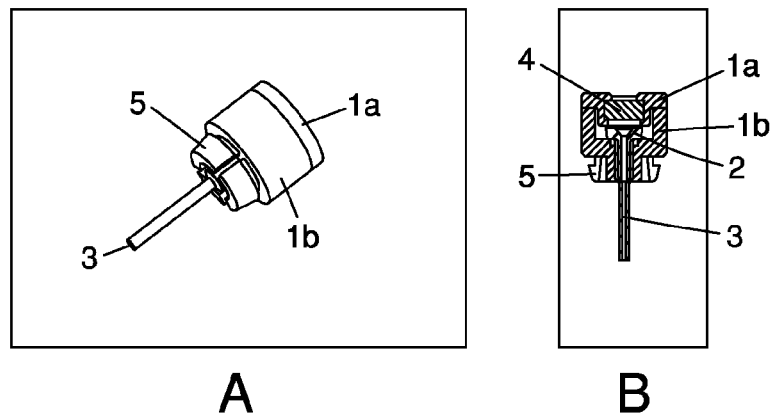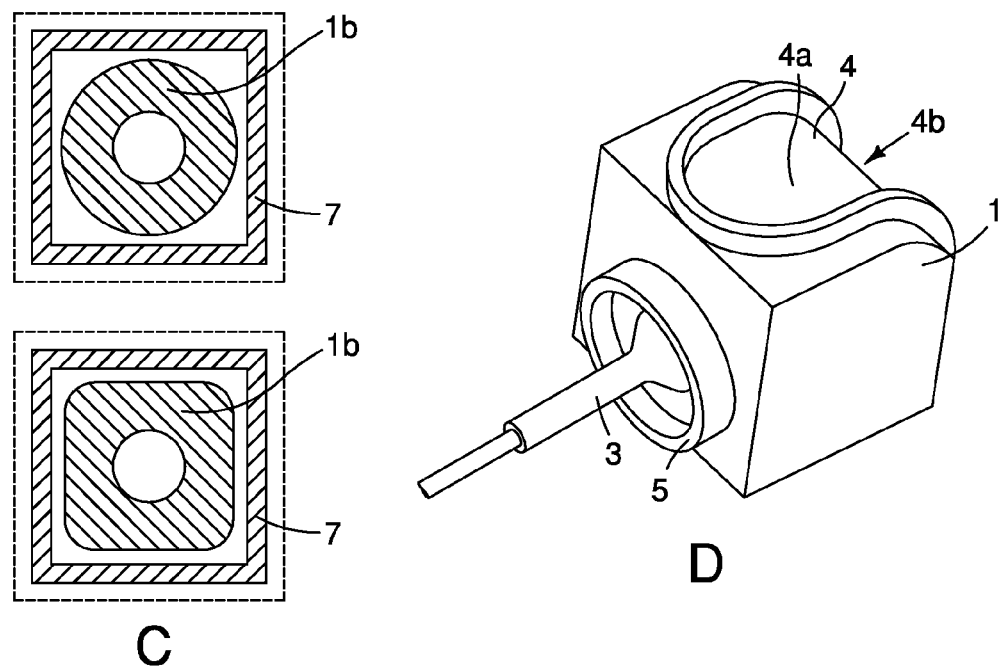
Fig. 1

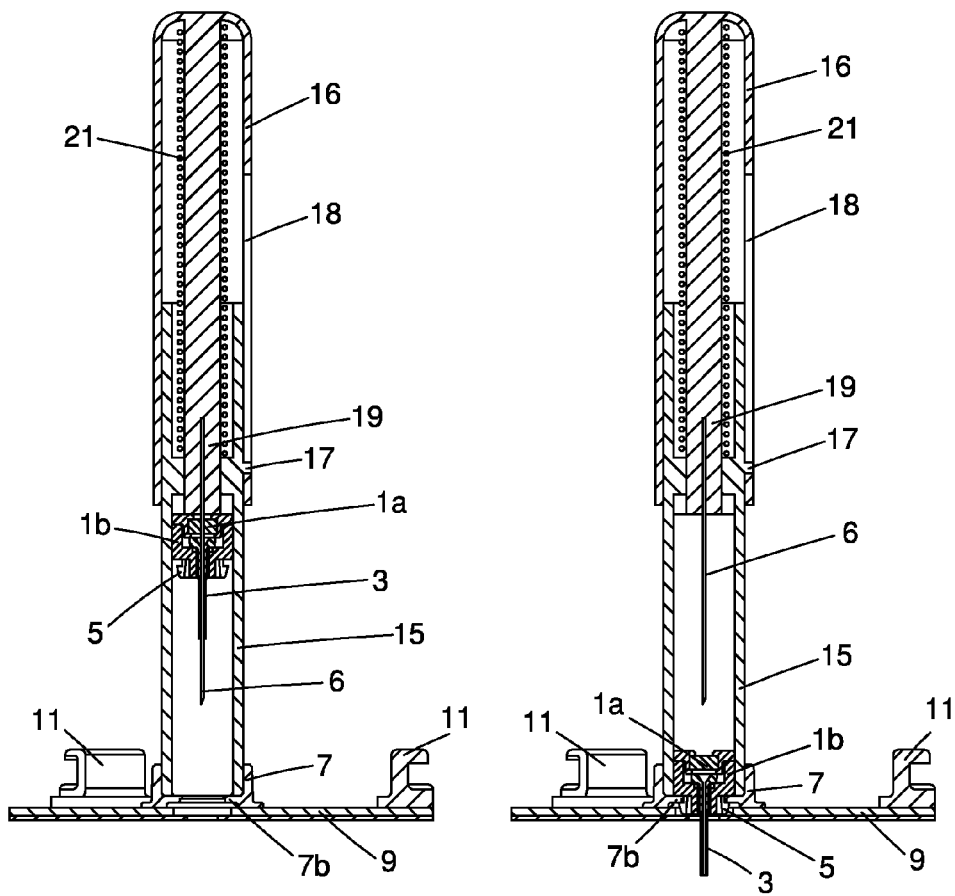

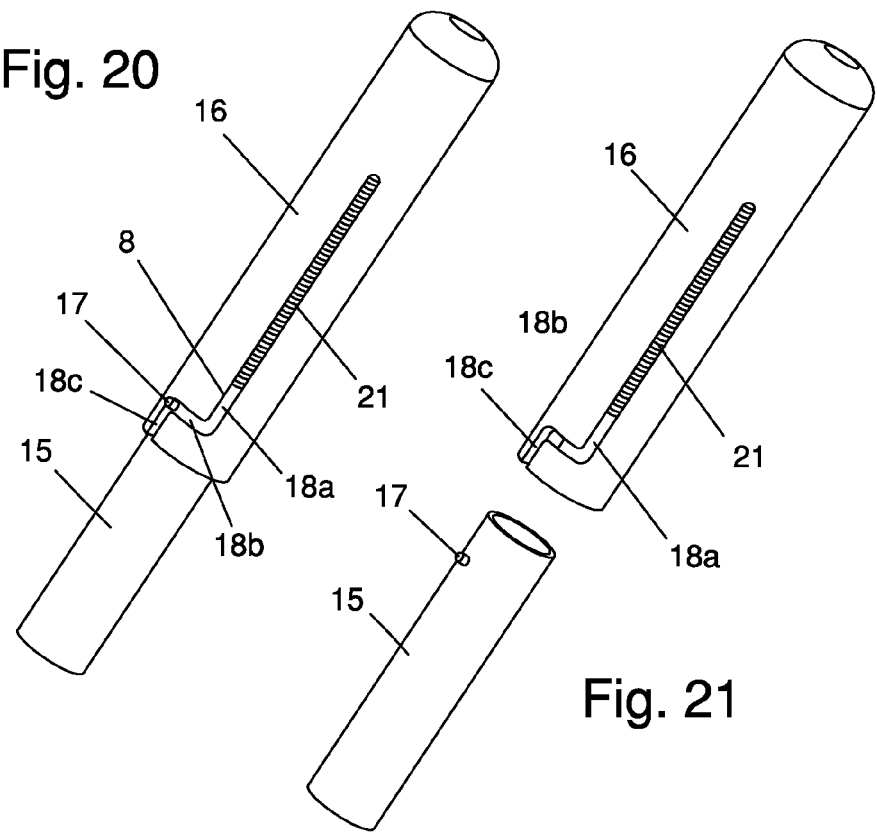
Fig. 20
Fig. 21
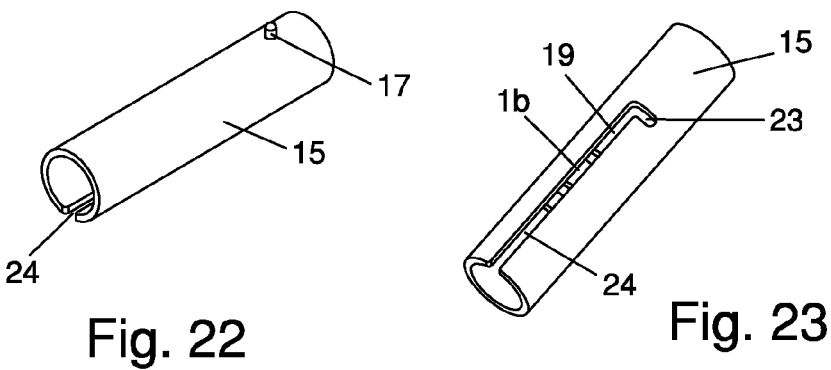
Fig. 22
Fig. 23

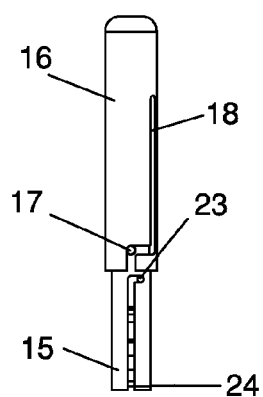 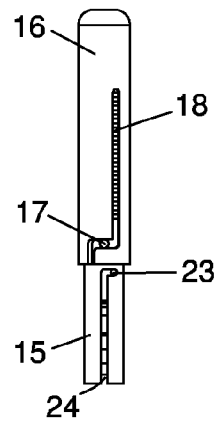 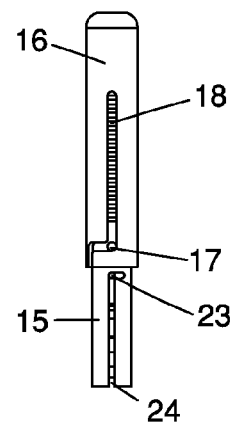
Fig. 24  Fig. 25  Fig. 26
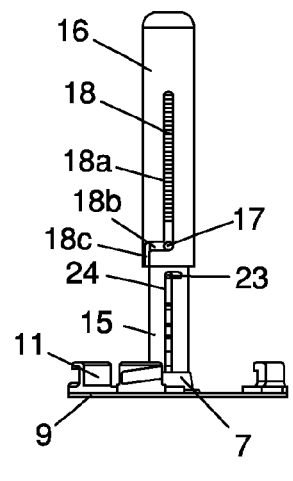 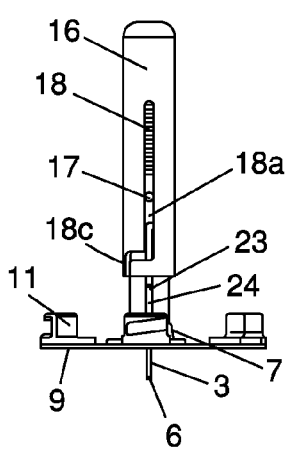 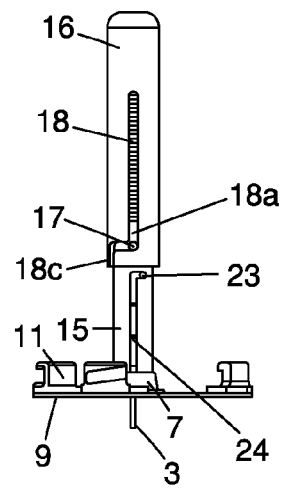
Fig. 27  Fig. 28  Fig. 29

CANNULA AND DELIVERY DEVICE

This application claims the benefit under 35 U.S.C. §371 of International Application No. PCT /DK2007/050103, filed Aug. 2, 2007, which claims the benefit of Danish Patent Application No. PA 2006 01027, filed Aug. 2, 2006, and U.S. Provisional Application Ser. No. 60/834,946, filed Aug. 2, 2006. These references are incorporated herein in their entirety.

The present invention relates to a cannula device for use in delivery devices or the like, and an inserter device for insertion of the cannula device.

PRIOR ART

Often delivery devices for intermittent or continuous administration of a therapeutical substance, such as insulin, are in form of a two-part device. Such a traditional delivery device comprises a base part having a cannula for subcutaneous insertion into a patient and comprising means for fastening of the base part to the patients skin, further the base part has means for closing of fluid access to the base part and it has means for opening of fluid access e.g. for receiving a connector cannula extending from a connector part and for bringing the connector cannula into fluid communication with the cannula of the base part. Often, the connector part is in fluid communication with a drug delivery device, e.g. an insulin pump.

Different kinds of delivery devices are described in WO 02/068014 A2, EP 0 956 879 A1, U.S. Pat. No. 5,522,803, US 2003/0225373 A1 and WO 03/026728 A1.

US 2003/0176852A1 discloses a delivery device in which a base part comprises a pivoting member, said base part comprising a cannula for insertion into a patient and pivoting member has an inner cavity with one receiving end adapted to receive an inserter needle or a connector cannula and two connecting ends (316I and 320) for further connection with the cannula of the base part. During insertion the pivoting member is positioned orthogonal to the base part and an inserter needle penetrates a membrane in the receiving end and the needle passes through a canal and through the first connecting end into the cannula which then can be inserted. After insertion the needle is removed and the pivoting member is connected with a connector. The connector and the pivoting member are connected from the same direction as the connection between the pivoting member and the inserter. The pivoting member is then turned in order for the second connecting end to align with the cannula. This device has the drawback that it is very sensitive to movement of the pivoting member since a small tuning will close of the delivery of drugs.

WO 02/094352 A2 discloses a delivery device having in the base part a construction that makes it possible to receive an insertion needle from one direction and a connector needle from a second direction. This design does not allow the patient to choose from which direction he/she wants to connect the connector with the base part.

In these prior art delivery devices the construction of the cannula and the means for providing fluid communication between the cannula and the cannula from the connector is unique for each set. Normally each infusion set also utilizes a specific set of guiding and/or locking means thus allowing only for a specific connector to engage with the base part.

WO 06/015600 A1 discloses a delivery device having a universal part having a cannula and means adapted to receive the cannula from the connector and fitting to most/all common infusion sets were available. This design allows for different types of connectors to be used with the same base part and visa versa, and it will also be possible to connect the connector from different angles.

The object of the present invention is to provide a cannula device which can be used as a component in different types of delivery devices and which is applied after a base part has been applied to the patient's skin.

According to the invention there is provided a cannula device for mounting in a base part comprising a housing and at least one membrane together defining at least one cavity, the cannula device further comprises a cannula mounted in the housing and being in fluid communication with the at least one cavity, which cannula device is provided with means for attaching the device to the base part on the proximal side of the device.

The advantage of such a cannula device is that it can be used as a standard component in delivery devices whether the delivery device has inclined or orthogonal insertion of the cannula. Thus this standard component can be mass produced and be used as a component in series of desired designs of the delivery devices. This results in lower manufacturing costs, a more flexible production line and a more flexible product. The positioning of the attaching means on the proximal side, i.e. the side turned towards the patient after mounting, of the device makes it easier to position the cannula device correctly by insertion as it is possible to cover or connect the sides of the cannula device with a handle or inserter device. Thus the attaching means will assure the attachment to the base part or receiving part while the side parts of the attaching means will assure the adaptation to the insertion device.

In another embodiment the cannula device for mounting in a base part comprises a housing and at least one membrane together defining at least one cavity, the cannula device further comprises a cannula mounted in the housing and being in fluid communication with the at least one cavity, where the cannula device is provided with means for attaching the cannula device unreleasably to the base part, i.e. to a specially adapted receiving portion of the base part.

The cannula device is normally a disposable device which is thrown away after use as the cannula is in contact with the patient's blood. If the base part to which the cannula device is attached also is a disposable device with approximately the same operating life it will not be necessary to be able to remove the device from the base part as both cannula device and base part will be removed and disposed of normally after having been used for a few days. When it is not possible to remove the cannula device from the base part it is not possible to have a used cannula device confused with a new sterile cannula device and it will also be evident that the receiving portion of the base part in which a cannula device is locked is not suitable for use.

If the base part is of a type which can be attached to the patient for a longer period, it might be possible to insert a new cannula device at a different position while the used cannula device is removed from the subcutaneous position e.g. by removing the cannula device together with a receiving portion or a part of a receiving portion to which it might be permanently attached.

Both embodiments have the advantage that it is possible for the user first to carefully position the base part, and after having positioned the base part properly, then the user can concentrate on injecting the cannula device.

In one embodiment the means for attaching the device to the base part comprise mechanical features cooperating with corresponding means on the base part, e.g. the means for attaching the device to the base part comprise parts extending from a proximal surface of the cannula device which parts can pivot and thereby temporarily reduce the diameter in at least one position or the means for attaching the device to the base part can comprise an adhesive surface on a proximal surface of the cannula device adhering to a corresponding surface of the base part.

In one embodiment the cannula device is provided with guiding means corresponding to an inserter device which guiding means secure a well-defined motion of the cannula device when being moved towards the base part by the inserter device.

In one embodiment the cannula device is inserted with an inserter device provided with a covering part covering the full length of the cannula device.

In one embodiment the part of the body of the cannula device having the largest diameter is rotational-symmetrical around a central axis.

In another embodiment the part of the body of the cannula device having the largest diameter has angled sides e.g. providing a triangular or quadrangular profile when cut-through. When having angled sides the profile of the cannula device can be used to define the correct insertion position.

In one embodiment the cannula device comprise a body showing a smooth outer surface and having an inner cavity, the inner cavity is at the distal end covered with a wall such as a membrane or a septum which can be penetrated by a needle such as a connector needle or a syringe and at the proximal end of the inner cavity a cannula is embedded, the outer proximal surface of the body, i.e. a surface of the body facing the receiving portion during injection of the cannula device, is provided with means for unreleasably attaching the device to a receiving portion. The smooth outer surface can e.g. have a round or oval circumference and the wall covering the distal end of the inner cavity can be penetrated by either by a pointy or by a blunt needle which ever might be preferred.

In one embodiment the unreleasable attachment between the receiving portion and the cannula device is formed automatically, that is without the need to take any action in order to form the unreleasable attachment, as the cannula device is pushed against the receiving portion.

According to another aspect of the present invention, a delivery device is provided. The delivery device includes a base part provided with a receiving portion for a cannula device where the receiving section has guiding means for an inserter device which inserter device holds the cannula device before insertion, i.e. the receiving portion has no guiding means for the cannula device or at least the receiving portion does not need guiding means for the cannula device as the guiding means for the inserter device might provide sufficient guidance for correct positioning of the cannula device.

In one embodiment the cannula device corresponds to an internal opening in a part of the inserter and the cannula device is provided with means for attaching the device to the base part on the proximal side of the body of the cannula device.

The cannula device will be described in further detail with reference to the figures:

FIG. 1A is a view of an embodiment of the cannula device of the present invention, B is a cut-through view of the same cannula device as shown in A, C is a cut-through view along line A-A of FIG. 1B of a cannula device having a square profile, D shows a cannula device having a square profile and to access positions from different angles;

FIG. 15 is a cross-sectional view of a two-unit insertion device and a cannula device in a position where the cannula device is mounted in the insertion device ready to be inserted;

FIG. 16 is a cross-sectional view of an insertion device and a cannula device in a position where the cannula device is inserted by the insertion device;

FIG. 20 is a perspective view of a two-unit, multiple-use insertion device, showing the disposable and reusable parts in a interconnected state;

FIG. 21 is a perspective view of a two-unit insertion device for multiple-use, showing the disposable and reusable parts in a disconnected state;

FIG. 22 is a perspective view of one side of a disposable part of a two-unit, multiple-use insertion device;

FIG. 23 is a perspective view of another side of a disposable part of a two-unit, multiple-use insertion device;

FIG. 24 is a side view of a two-unit, multiple-use insertion device in which the disposal and reusable parts are being intereconnected together;

FIG. 25 is a side view of a two-unit, multiple-use insertion device in which the disposal and reusable parts are being interconnected together;

FIG. 26 is a side view of a two-unit, multiple-use insertion device in which the disposal and reusable parts are interconnected together;

FIG. 27 is a side view of the two-unit, multiple-use insertion device in FIGS. 24-26, particularly illustrating the insertion device as mounted on a base part and ready to insert a cannula;

FIG. 28 is a side view of the two-unit, multiple-use insertion device in FIG. 27, particularly illustrating the insertion device in a position after the insertion needle has been fully inserted subcutaneously into a patient;

FIG. 29 is a side view of the two-unit, multiple-use insertion device in FIG. 27, particularly illustrating the insertion device in a position after the insertion needle has been release from the cannula.

DETAILED DESCRIPTION OF THE INVENTION

Figure 2:
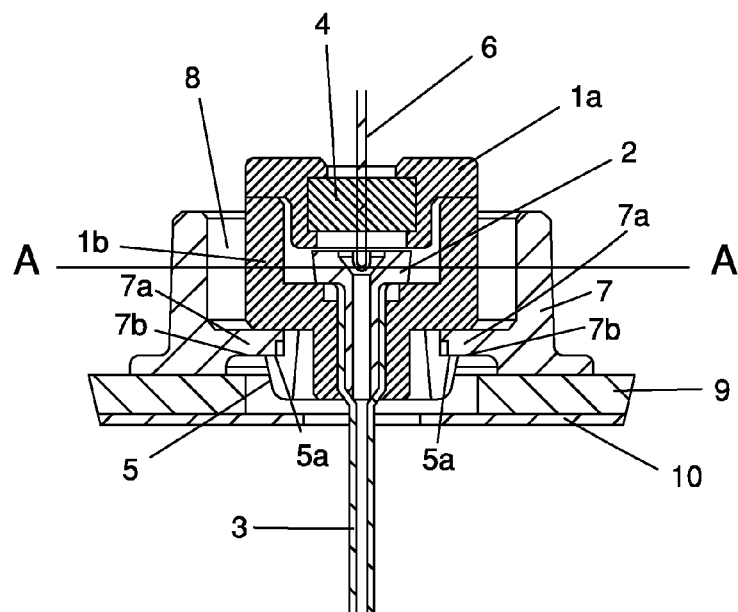
FIG. 2 is a cut-through view of an embodiment of the cannula device of the present invention placed in a receiving portion of a delivery device.

FIGS. 1 A and B show a first embodiment of the present invention. In this embodiment, the cannula device includes a housing 1a, 1b and a wall in the form of e.g. a membrane 4 which together define an inner cavity adapted to receive a piercing member 6 extending from e.g. a connector or a syringe.

The housing 1a, 1b is normally made of a relatively hard molded plastic material.

The lower part 1b can be constructed of a cylindrical upper part where the inner surface forms the walls of the inner cavity and the outer surface is smooth and without protrusions, and of a cylindrical lower part with a smaller diameter where the inner surface forms an opening which supports a cannula 3 and the outer surface comprise means 5 for attaching the cannula device unreleasably to a base part 9.

The cannula device can also be constructed with an angular profile e.g. a quadrangular profile as shown in FIG. 1C. This figure shows two embodiments of the cannula device: a device having a round profile (upper) and a device having a square profile (lower). This profile will show if the cannula device is seen from above along the line A-A shown in FIG. 2. Whether the profile of the cannula device is round or angular it might have a loose fit or a close fit in the receiving portion where a loose fit means that the receiving section is provided with guiding means for the inserter and the cannula device is placed in correct position when the inserter is placed according to the guiding means and when the inserter is removed from the receiving section an empty space corresponding to the walls of the inserter will appear around the cannula device. A close fit means that the receiving section of the base part is provided with a room closely corresponding to the form or the profile of the cannula device and the inserter positions the cannula device inside the room having walls closely corresponding to the outer walls of the cannula device.

The cannula device shown in FIG. 1D has two access openings covered with one membrane 4, in another (not shown) embodiment each access opening could be covered with separate non-connected membranes at different surface positions (e.g. respectively 4a and 4b). This cannula device can be fed with medication from two different angles via the surface 4a or the surface 4b. Such a device provides the possibility of having an extra access for medication if a corresponding opening is provided in the receiving portion 7 or alternatively the cannula device could be a standard for two different types of base parts 9 having different openings in the receiving portion 7.

The cannula is made of a soft inert material and in this embodiment the cannula 3 is attached to the housing 1b by pushing a fastening part 2 made of a more rigid material than the cannula 3 into the opening of the cylindrical lower part after positioning the cannula 3 in the opening. As the fastening part 2 is pushed into the opening the cannula 3 will be squeezed against the walls of the opening and this pressure will keep the cannula 3 in a correct position.

The means 5 for attaching the cannula device unreleasably to the base part 9 is in this embodiment constructed as several hooks 5; these hooks 5 can pivot around the position where they are attached to the housing 1a, in this embodiment the attachments for the hooks 5 are of a flexible material i.e. the hooks can be pushed inwards when the hooks 5 pass an area of reduced diameter. Each hook 5 is provided with an upper surface 5a parallel to a contact surface 7b of a receiving portion 7 of the base part 9. Each hook 5 is also provided with an inclined surface 5b which inclined surface during insertion of the cannula device is in contact with a protruding part 7a of the receiving portion 7. When the cannula device is pushed down into the receiving portion 7 the hooks 5 are pushed inward against the lower cylindrical part of the housing 1b and as the hooks 5 in this position are biased, the hooks 5 will return to their original position when the inclined surface 5b of the hooks 5 has fully passed the protruding part 7a of the receiving portion 7. When the hooks 5 return to their original position the upper surface 5a of the hooks will be in touch with the contact surfaces 7b of the receiving portion 7 and the cannula device will be locked in this position as neither the cannula device nor the receiving portion 7 are provided with means to push the hooks 5 inward against the lower cylindrical part of the housing 1b.

According to another not shown embodiment either the upper side of the protruding parts 7a or the lower side of the housing 1a is provided with an adhesive which adhesive then works as unreleasably attaching means when the cannula device is pushed into position in the receiving portion 7.

FIG. 2 shows the same embodiment of the cannula device as in FIG. 1, where the cannula device is positioned in the receiving portion 7. The receiving portion 7 is provided with essentially vertically positioned walls covering the side section of the cannula device and a bottom part formed by the protruding parts 7a on which the cannula device rests when locked in the receiving portion 7. The space 8 around the cannula device which has the form of a cylindrical room between the essentially vertical walls and the side section of the cannula device creates a guiding mean for an inserter. The cannula device is in this embodiment normally fully covered by a lower cylindrical part of the inserter and when the user wants to inject the cannula device, the cylindrical lower part of the inserter is placed in the space 8 formed by the receiving portion 7 and then the cannula device is pushed in position by a plunger being moved forward inside the cylindrical lower part of the inserter.

The receiving portion 7 is attached unreleasably to the base part 9 which base part 9 is fastened to the skin of a patient e.g. with a mounting pad 10.

Figure 3:
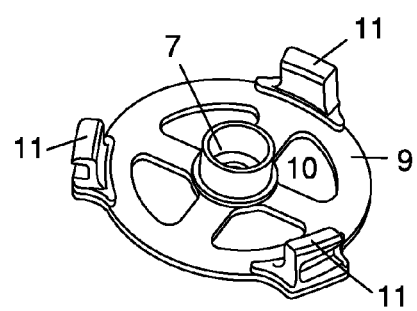
FIG. 3 is a view from above of a base part with a receiving portion in the center.

FIG. 3 shows an upper view of a base part 9 provided with a receiving portion 7 and with attachment parts 11 for a delivery part 12.

Figure 4:
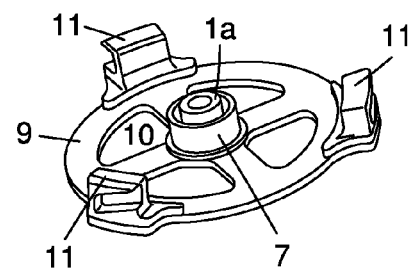
FIG. 4 is a view from above of a base part with a receiving portion in the center and a cannula device with a round profile positioned in the receiving portion.

FIG. 4 shows an upper view of the same base part 9 as shown in FIG. 3 also provided with a receiving portion 7 and with attachment parts 11 for a delivery part 12 but in FIG. 4 a cannula device has been positioned in the receiving portion 7.

Figure 5:
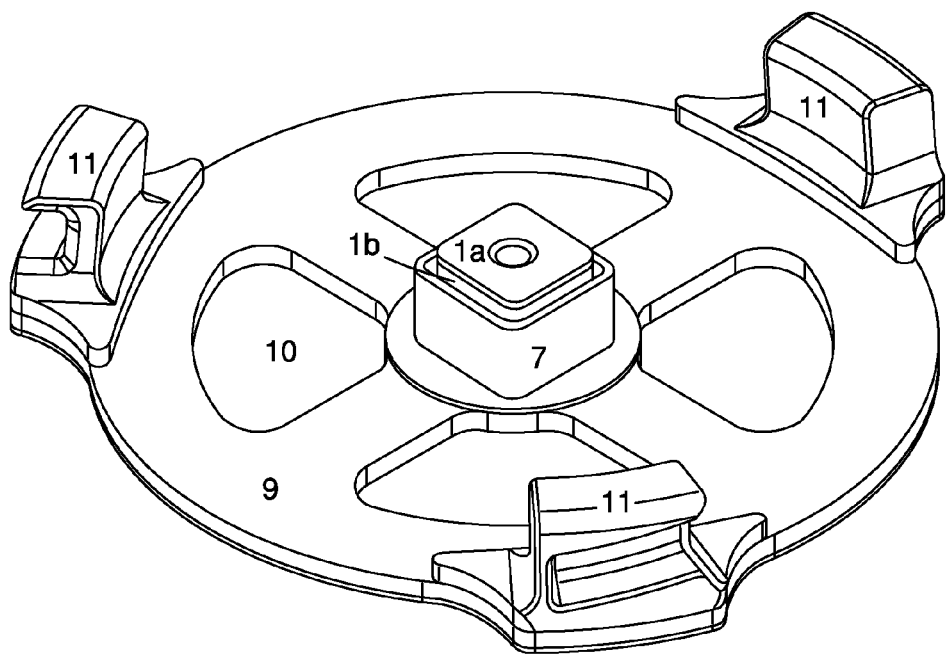
FIG. 5 is a view from above of a base part with a receiving portion in the center and a cannula device with a square profile positioned in the receiving section.

FIG. 5 shows an upper view of another embodiment of a base part 9. The receiving section 7 of this base part 9 has a square inner room and a cannula device 1a having an outer square profile is placed in the receiving section 7.

Figure 6:
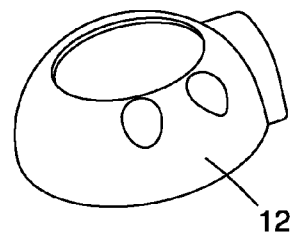
FIG. 6 is a view from above of a base part on which a top comprising a reservoir and means for transporting the content of the reservoir to the patient has been mounted.

FIG. 6 shows an upper view of a base part 9 as shown in FIG. 3, 4 or 5 but in FIG. 6 the base part 9 has been provided with a cover 12 in which a reservoir 13 for medication and means for transporting of the medication from the reservoir to the patient are embedded.

Figure 7:
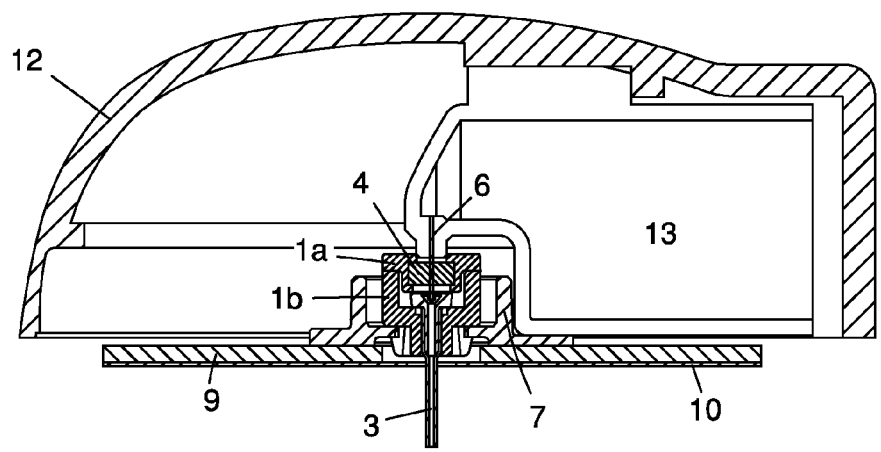
FIG. 7 is a cut-through view of the delivery device shown in FIG. 5.

FIG. 7 shows a cut-through view of the device shown in FIG. 6. FIG. 7 shows a receiving portion 7 positioned on a base part 9 which base part 9 has an underlying mounting pad 10. A cannula device has been inserted in the receiving portion 7 and the cannula 3 of the cannula device is inserted subcutaneously in a patient. The cannula device and the receiving portion could be either square or round. A cover 12 has been mounted on the base part 9, and a connector needle 6 forms a fluid connection between a reservoir 13 which is attached to the inside of the cover 12 and the cannula device by penetrating the septum 4 of the cannula device.

The delivery device of FIG. 7 can be mounted on the patient through the following steps:

I. A sterile base part 9 is unpacked and secured to the skin of the patient.
II. A sterile single-use inserter including a cannula device is unpacked or a sterile part comprising an injection needle combined with a cannula device is unpacked an applied to a multiple-use inserter, the proximal end of the inserter is placed in the guiding means 8 of the receiving portion 7 and the cannula device is inserted, i.e. the cannula 3 is injected subcutaneously.
III. A delivery part comprising a cover 12, a reservoir 13 and means for transporting the content of the reservoir to the patient is fastened to the base part 9, and when the cover 12 is fastened to the base part 9 the connector needle 6 penetrates the septum 4 of the cannula device and then the delivery device is ready to work.

Figure 8:
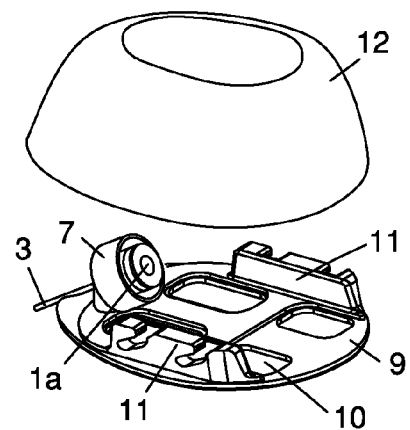
FIG. 8 is a cut-through view of another embodiment of a delivery device according to the invention.

FIG. 8 shows another embodiment of a delivery device. In this embodiment the receiving portion 7 is positioned at the edge of the base part 9 and the cannula device having a cylindrical body 1b is not inserted perpendicular to the patient's skin but in an angle of approximately 30°. The reference numbers refers to similar parts as in FIGS. 6 and 7.

Figure 9:
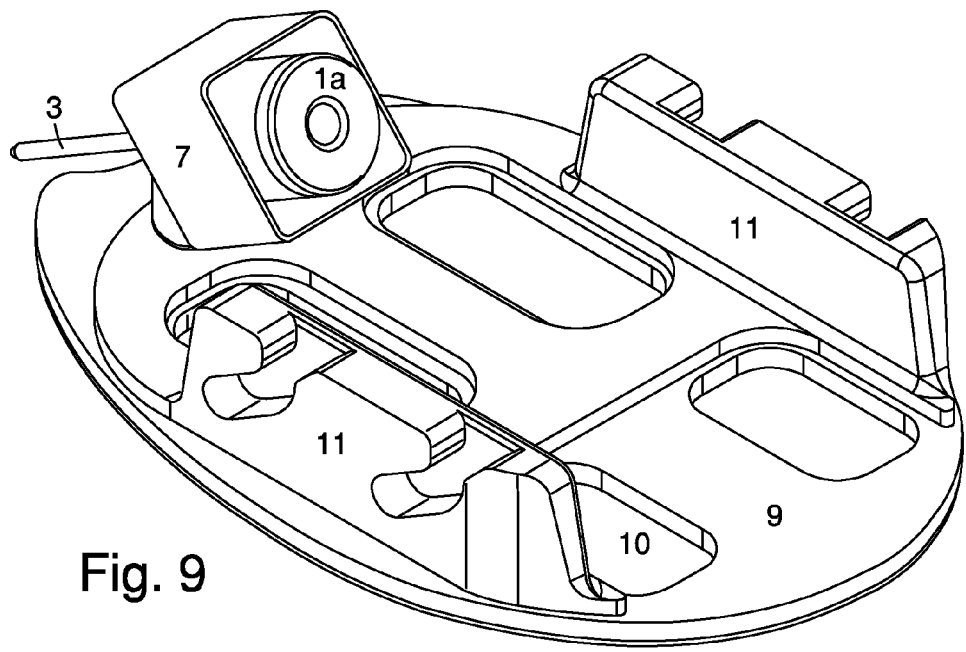
FIG. 9 shows a base part of an embodiment having a loose fit square receiving section for a round cannula device.
Figure 10:
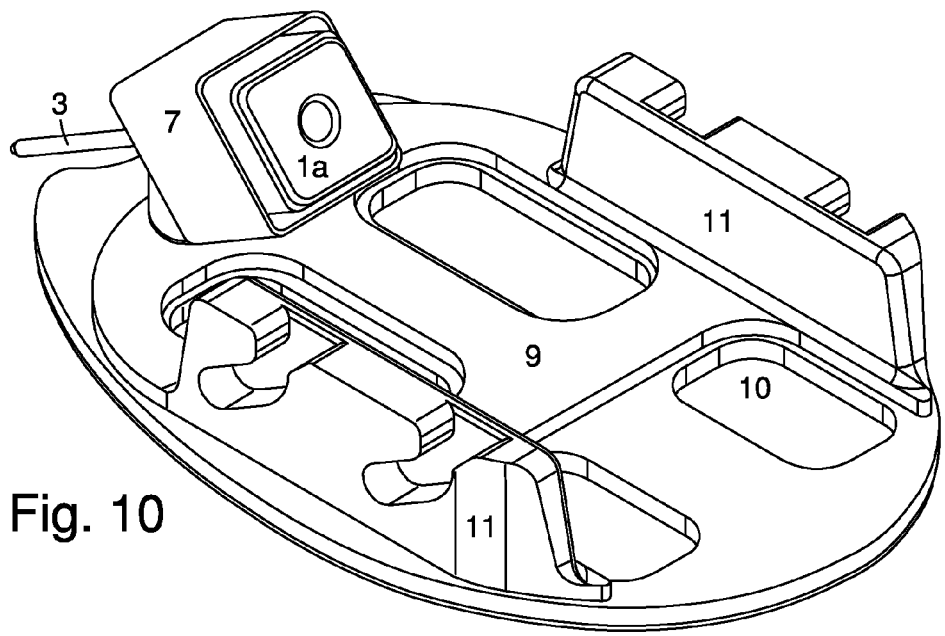
FIG. 10 shows a base part of an embodiment having a close fit square receiving section for a square cannula device.
Figure 10A:
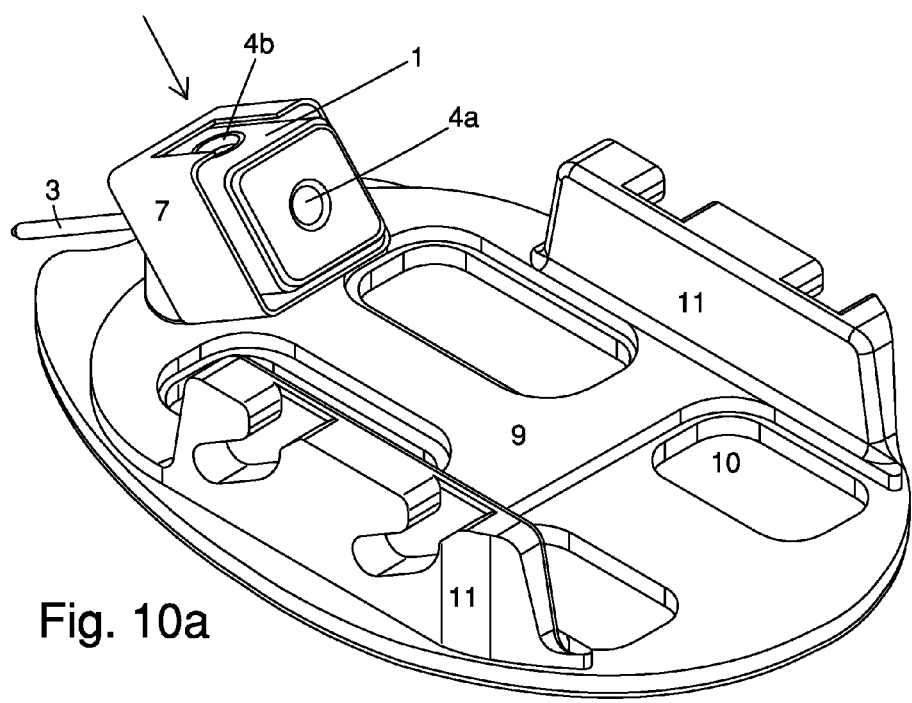
FIG. 10A shows a base part of an embodiment having a close fit square receiving section for a square cannula device which cannula device has two inlets.

FIGS. 9 and 10 shows other embodiments of a delivery device. The embodiment of FIG. 9 is provided with a cylindrical cannula device (round profile) placed in a square or rectangular receiving portion 7. This embodiment provides a loose fit for the cannula device. The embodiment of FIG. 10 is provided with a square or rectangular cannula device placed in a square or rectangular receiving portion 7. This embodiment also provides a loose fit for the cannula device where the upright walls of the receiving portion 7 can provide the guiding means for an inserter. FIG. 10a shows how the embodiment of FIG. 10 can be adapted for a cannula device having to membrane covered inlets 4a and 4b.

Figure 11:
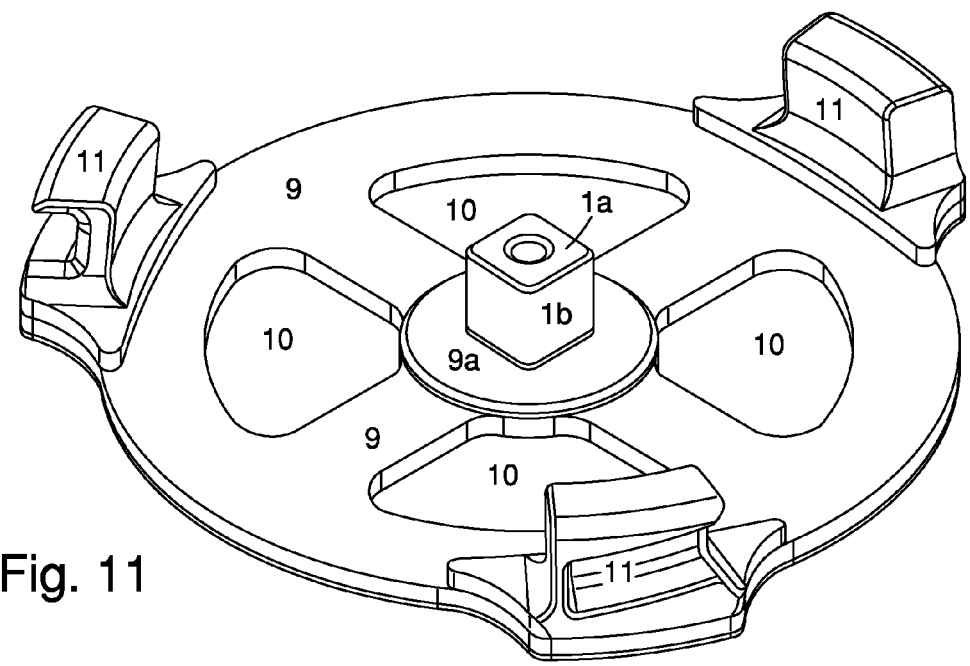
FIG. 11 shows a base part of an embodiment having a receiving section without upright walls for any cannula device.

FIG. 11 shows a centrally placed receiving portion 7 without upright walls guiding the inserter into position. Instead the slightly raised circumference of the central plate 9a of the base part 9 corresponding to a part of the proximal end of the inserter indicates the correct position of the inserter during insertion of the cannula device 1.

Figure 12:
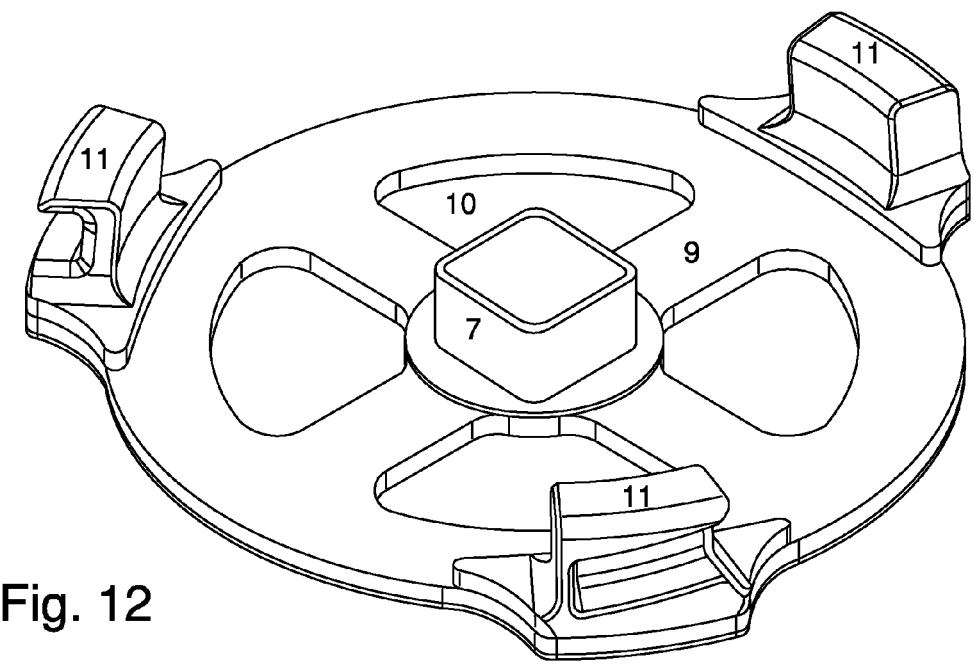
FIG. 12 shows a base part of an embodiment having a square receiving section for a not shown cannula device.

FIG. 12 shows a base part 9 having a centrally placed receiving portion 7 having upright walls which walls provide the receiving portion 7 with a square profile. The base part 9 is shown before the cannula device 1 is inserted.

Figure 13:
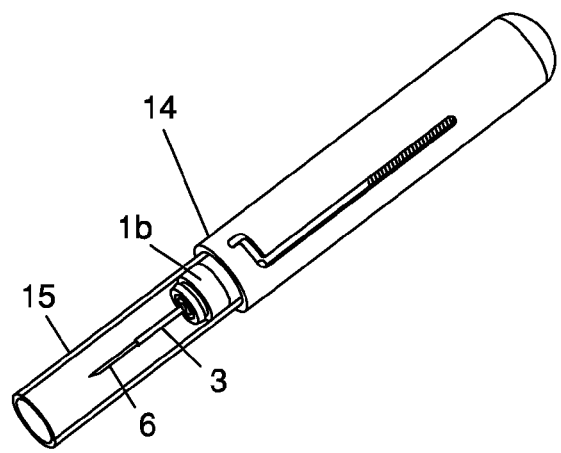
FIG. 13 is a side view showing the cannula device mounted in an inserter prepared for injection.
Figure 14:
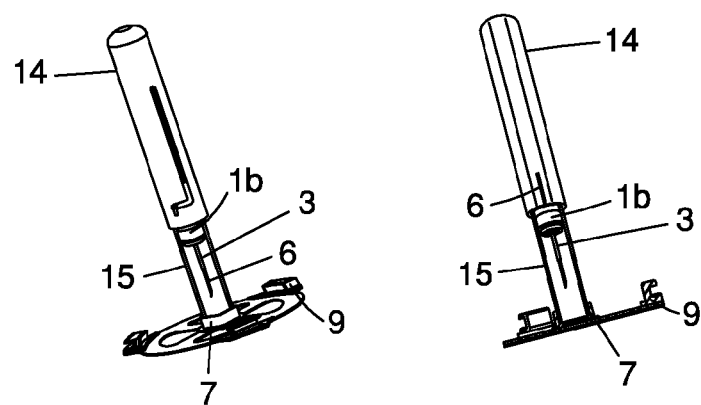
FIG. 14 shows two views of the same embodiment of a cannula according to the invention mounted in an inserter which inserter is joined to a receiving portion of a base part.

FIGS. 13 and 14 illustrates an inserter which can be used when inserting the cannula device in a delivery device with a receiving portion 7 shown in FIG. 3-10. Such an inserter should have outer walls providing a profile corresponding to a part e.g. the walls of the receiving portion 7 and inner walls providing a profile corresponding to the cannula device in question in order for the inserter to guide the cannula device into the correct position.

In order for the inserter 14 to interact properly with the receiving portion 7 of the base part 9 it is desirable that the inserter 14 is provided with guiding means 15 which extents beyond the end of the injection needle of the inserter. The guiding means 15 can have a triple purpose as they can serve 1) to keep the injection needle out of sight of the user before, during and after injection of the cannula device, 2) to protect the environment from the injection needle, and 3) to assure safe and precise injection of the cannula device into the receiving portion 7.

In this embodiment the guiding means 15 of the inserter has a form which corresponds to the shape of the guiding means 8 in the receiving portion 7, e.g. of a cylindrical or rectangular tube.

A more detailed description of the specific inserter shown in FIGS. 8 and 9 and how this inserter functions can be found in DK application no. PA200601028 filed on 2 Aug. 2006.

FIGS. 15 and 16 show a more detailed view of the insertion device and in FIG. 15 the insertion device is in a position where it is ready to be activated but not yet activated and in FIG. 16 the insertion device is in a position after activation and after insertion of the cannula device. The embodiment of the insertion device in FIGS. 15 and 16 comprises guiding means in the form of a first insertion part and a second insertion part 16, the first insertion part 15 is mounted slidably within the second insertion part 16 via guiding means in the form of a tap 17 sliding in slit 18, it further comprises a needle-holding part 19 comprising an injection needle 6 and an elastic element 21 which in this embodiment supports retraction of the injection needle 6 after insertion of the cannula device. The injection needle 6 is joined to the cannula device in such a way that the cannula 3 is inserted subcutaneously into the skin of a patient when the inserter device is activated. In the shown embodiment the injection needle 6 is placed inside the hollow cannula 3. The elastic element 21 rests respectively on an interior downward top surface of the second insertion part 16 and on an interior upward surface of the first insertion part 15 and pushes the two parts away from each other when the elastic element 21 is biased. In FIGS. 15 and 16 the elastic element 21 is unbiased.

In this embodiment the insertion device is positioned in the receiving portion 7 on a base part 9 before it is activated. On the base part 9 the insertion device is releasably connected to the receiving portion 7, which is mounted on the base part 9, and the hooks 5 of the cannula device can engage with the contact surface 7b formed in the receiving portion 7 and thereby lock the cannula device to the base part 9. The base part 9 is fastened to the patient's skin e.g. by an adhesive layer.

The embodiment of the inserter device shown in FIGS. 1 and 2 is intended for single-use of the whole of the insertion device. The embodiment makes it possible first to carefully position a base plate 9 e.g. comprising a receiving portion 7 on the skin of the patient, second to insert the cannula device by positioning the insertion device in the receiving portion 7 and third to remove the insertion device from the receiving portion 7 and dispose of the inserter device including the used injection needle 6. According to this embodiment the injection needle 6 is never visible to the user and at the same time the first insertion part 15 protects the surroundings from the pointy and potentially infected injection needle 6.

The embodiment of the insertion device of FIGS. 15 and 16 is a two-part unit which two units interact via an elastic element 21 (a spring); each unit can be constructed of a moulded body. The first unit is constituted by the first insertion part i.e. the guiding means 15 and the second unit is constituted by the second insertion part 16 and the outer walls of both parts are formed as cylindrical tubes. The first insertion part 15 slides within the second insertion part 16 and the second insertion part 16 is provided with a central plunger part comprising the needle-holding part 19 which slides within the first insertion part 15. The tubes can have any cross-sectional form e.g. oval or polygonal such as hexagonal or octagonal or any other form as long as the first insertion part 15 can move along the longitudinal axis of the second insertion part 16. On delivery this single-use insertion device can either be joined to the receiving portion 7 or packed along. If the single-use equipment is joined to the receiving portion 7, then the user first positions the base plate 9 on the skin of the patient and then the user activates the insertion device by unlocking the second insertion part 16 from the first insertion part 15 and then push the second insertion part 16 toward the patients skin. If the single-use inserter device is packed alone, then the user first choose a base plate 9 with a receiving portion 7 and then positions the base plate 9 on the patients skin, then the user unpack the insertion device and place the insertion device in the receiving portion 7 on the base plate. Finally the user injects the cannula device 1b into the receiving portion 7, remove the inserter device from the base plate 9, lock the first and second insertion parts 15 and 16 in relation to each other in order to protect the surroundings from the contaminated insertion needle 6 and dispose of the complete inserter device in a safe way.

The second insertion part 16 is releasably fastened to the cannula device 1b and unreleasably fastened to the needle-holding part 19 carrying the injection needle 6 for penetrating the skin of a patient. In this embodiment the elastic element 21 is illustrated by a helix metal spring, but the elastic element 21 may be in any form, e.g. a rubber cylinder or the like, which can be positioned between the two insertion parts 15 and 16 and provide the desired action between the two parts. When the insertion device is in the position it reaches before and after activation as shown in FIGS. 15 and 16, the elastic element 21 is unbiased and when the insertion device is activated by manually pressing down the second insertion part 16 to a forward position for insertion of the cannula device, the elastic element 21 is biased as long as the second insertion part 16 is in the forward position.

Figure 17:
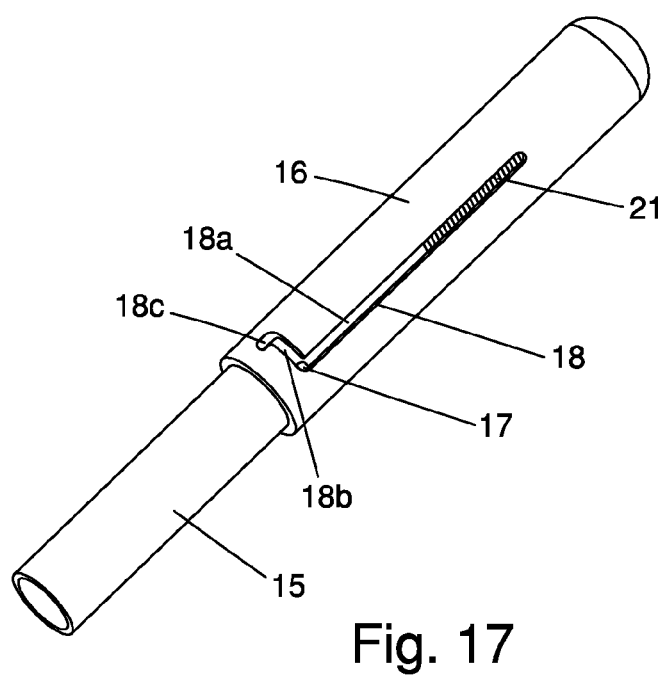
FIG. 17 is a perspective view of a two-unit insertion device, particularly illustrating the exterior surface of the insertion device.

As shown in detail in FIG. 17, the exterior surface of the first insertion part 15 is provided with a protrusion formed as a cylindrical tap 17 protruding from the outer surface of the first insertion part 15. The tap 17 interacts with an opening in the form of a slit 18 in the second insertion part 16, said slit 18 is shaped with three parts 18a, 18b and 18c where the first part 18a has a direction along the longitudinal axis of the second insertion part 16, the second part 18b is perpendicular to the longitudinal axis of the second insertion part 16, and the third part 18c also has a direction along the longitudinal axis of the second insertion part 16. The third part 18c is connected to the second part 18b opposite the connection between the second part 18b and the first part 18a. When the tap 17 of the first insertion part 15 is placed in a locking position in the slit 18, then the tap 17 is positioned in the third part 18c of the slit 18 and the spring 21 is either unbiased or only slightly biased and the insertion parts 15 and 16 are locked in relation to each other. When the user needs to activate the device the second insertion part 16 is pushed slightly down until the tap 17 hits the upper wall of the second part 18b of the slit and the user feels it is not possible to push the second insertion part 16 further down, at this point the tap 17 is brought into level with the second part 18b of the slit 8. The user then turns the second insertion part 16 to the right until the tap 17 hits the right wall of the first part 18a of the slit 18 and the user again feels it is not possible to turn the second insertion part 16 any further, and at this position the insertion device is ready for activation.

Figure 18:
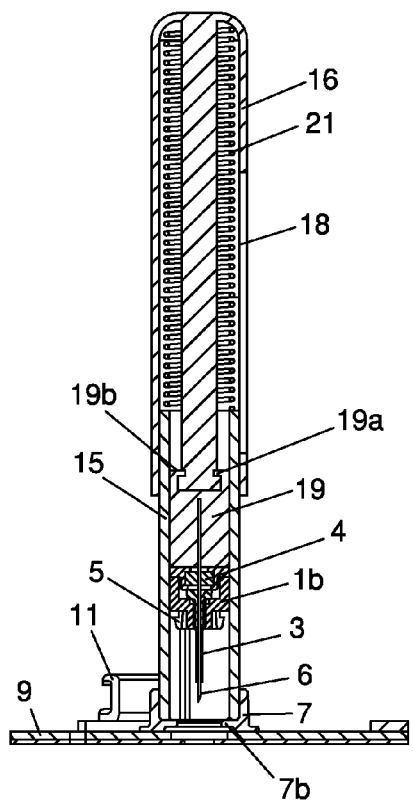
FIG. 18 is a cross-sectional view of a two-unit, multiple-use insertion device and a cannula device in a position where the cannula device is mounted in the insertion device ready to be inserted.
Figure 19:
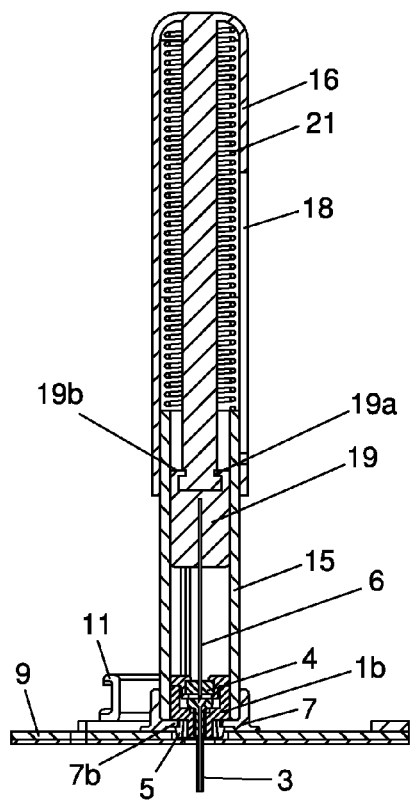
FIG. 19 is a cross-sectional view of a two-unit, multiple-use insertion device and a cannula device in a position where the cannula device is inserted by the insertion device.

The embodiment of the insertion device shown in FIGS. 18 and 19 is intended for multiple-use. FIG. 18 show the insertion device in a not yet activated position before insertion and FIG. 19 shows the insertion device in a position after activation, where the cannula 3 has been inserted and the injection needle 6 has been pulled back to the starting point.

The injection device according to the embodiment of FIGS. 18 and 19 comprises like the first embodiment a first insertion part 15 and a second insertion part 16 mounted similarly to each other as described for the first embodiment. A cannula device 1b is connected to a needle-holding part 19, which needle-holding part 19 is provided with an injection needle 6. In this embodiment the needle-holding part 19 is a separate unit, i.e. the needle-holding part 19 is releasably fastened to the second insertion part 16 by way of for example a tongue and groove connection 19a, 19b where a protruding part 19a extends into a groove part 19b. If the needle holding part 19 together with the first insertion part 15 is turned to the left the tongues 19a will be released from the grooves 19b and the needle holding part 19 can be removed from the second insertion part 16 covered by the outer walls of the first insertion part 15. Normally the needle holding part 19 is movably but unreleasably connected to the first insertion part 15. In FIGS. 18 and 19 the insertion device is releasably placed in the receiving portion 7 on the base part 9.

FIGS. 20 and 21 show in detail the interconnection of the two-unit insertion device of the present invention intended for multiple-use. The first insertion part 15 is like the embodiment of FIG. 15-17 provided with a protrusion 17 on the exterior or outer surface formed as a cylindrical tap and able to move in the slit 18. As described for the single-use embodiment the slit 18 comprises three stair-shaped parts, the first part 18a, the second part 18b and the third part 18c. The multiple-use embodiment of FIGS. 20 and 21 differs from the single-use embodiment in that the third part 18c of the slit 8 forms an opening in the cylindrical wall of the second insertion part 16 and this opening makes it possible for the tap 17 to leave the slit 18; the short third part 8a thereby provides means for joining or releasing the first insertion part 15 from the second insertion part 16.

When the insertion device is assembled, the tap 17 of the first insertion part 15 is positioned in the open third part 18c of the slit 8 and pushed upwards until the tap 17 reaches the second transverse part 18b of the slit 8. Then the second insertion part 16 is rotated until the tap 17 is positioned in the middle area of the second transverse part 18b of the slit 8 thereby placing the first and second insertion parts in positions which prevent longitudinal movements of the first insertion part 15 in relation to the second insertion part 16. The elastic element 21 is in this position unbiased or only slightly biased and the insertion device is prepared for use.

Likewise, the two-unit insertion device can be disassembled by reverse rotation of the second insertion part 16, thereby moving the tap 17 from the second transverse part 18b of the slit 8 into the third part 18c of the slit 8 and pulling the second insertion part 16 away from the first insertion part 15 as the tap 17 exit via the open end of the third part 18c thereby releasing the first insertion part 15 including the needle holding part 19 from the second insertion part 16.

This embodiment makes it possible to remove and dispose of only the first insertion part 15 including the needle holding part 19 and the used injection needle 6. This feature provides a possibility of repeated use of the second insertion part 16 together with a new replaced first insertion part 15 containing a new injection needle 6. Furthermore, this embodiment makes it possible for the first insertion part 15 to constitute a needle protector both before and after activation of the insertion device for insertion of the cannula device.

The two FIGS. 22 and 23 show in detail the first insertion part 15 of the multiple-use embodiment. FIG. 22 shows the side of the insertion part 15 comprising the tap 17 for engaging with the slit 18 of the second insertion part 16, FIG. 23 shows the opposite side of the first insertion part 15 comprising means in the form of a protruding tap 23 positioned on the needle holding part 19 which tap 23 engages with an essentially L-shaped slit 24 for locking and unlocking the needle-holding part 19 before and after insertion. The needle-holding part 19 comprises the injection needle 6 (not shown) and is releasably fastened to the cannula 1b.

FIGS. 24, 25 and 26 show the steps of mounting the replaceable first insertion part 15 in the insertion device intended for multiple-use. FIGS. 27, 28 and 29 show the insertion device at different positions during insertion of the cannula device into the base part 9.

FIG. 24 shows how the disposable first insertion part 15 is placed in a reusable second insertion part 16. The first insertion part 15 is guided into the third part 18c of the slit 8 by use of the tap 17. When the tap 17 is placed in the transverse second part 18b of the slit 8, as shown in FIG. 25, the first insertion part 15 is secured in a locked position in the longitudinal direction relative to the second insertion part 16 of the insertion device.

A protruding tap 23 of the needle-holding part 19 is engaged with a slit 24 in the wall of the first insertion part 15, and during positioning of the first insertion part 15 into the second insertion part 16, the protruding tap 23 is placed in a part of the L-shaped slit 24 where the movement in a longitudinal direction relative to the first insertion part 15 is not possible as the part of the slit 24 where the tap 23 is positioned only allows movement perpendicular to the longitudinal direction, i.e. the tap 23 secures the needle holding part 19 in a locked position and the injection needle 6 is therefore locked inside in the first insertion part 15 and kept safe and hidden to the patient.

In FIG. 25, the tap 17 of the first insertion part 15 is rotated towards the right thereby moving the tap 17 into the transverse second part 18b of the slit 18. The tap 23 of the needle-holding part 19 is due to the rotation of the first insertion part 15 simultaneously pushed into the short part of the L-shaped slit 24 where movement of the needle holding part 19 in a longitudinal direction is not possible. The elastic element 21 is unbiased in this position.

FIG. 26 shows the placing of tap 17 at the right end point of rotation of the first insertion part 15. After full rotation of the insertion part 1 the tap 17 has reached the corner between the first part 18a of the slit 18 and the second transverse part 18b and further rotation of the first insertion part 15 in relation to the second insertion part 16 is not possible. The tap 23 of the needle-holding part 19 is during the rotation of the first insertion part 15 simultaneously moved into the corner of the essentially L-shaped slit 24 leaving the needle-holding part 19 in an unlocked position relative to the longitudinal direction. The elastic element 21 is still in an unbiased position. Thus, the insertion device is left in a position ready for activation and insertion of insertion needle 6 combined with the cannula 3 of the cannula device.

FIG. 27 shows the same insertion device as FIG. 24-26 in a position ready for activation and insertion of the cannula 4, and the insertion device is mounted in a receiving portion 7 on a base part 9.

FIG. 28 shows the insertion device when fully activated i.e. the insertion needle 6 combined with the cannula 3 of the cannula device is fully inserted into the subcutaneously layer of the skin of the patient. During insertion the second insertion part 16 is manually pressed down towards the patient's skin, thereby biasing the elastic element 21 whereby the first insertion part 15 slides upwards into the internal space of the second insertion part 16 as the tap 17 is in an unlocked position. The manual pressure will cause tap 17 to slide upwards guided by the first part 18a of the slit 18 of the second insertion part 16 and tap 23 will slide upwards in the longitudinal slit 24 of the first insertion part 15 by which the injection needle 6 and cannula 3 exits the first insertion part 15. When exiting the first insertion part 15 the injection needle 6 penetrates the patients skin and inserts the cannula 3 subcutaneously. The cannula device engages with the receiving portion 7 on the base plate 9 assuring fastening of the cannula device to the receiving portion 7.

FIG. 28 shows the insertion device in a position after the insertion needle 6 has been fully inserted subcutaneously into a patient. The manual pressure on the second insertion part 16 has been at least partly released and the elastic element 21 is halfway to return to the unbiased position, this return to the unbiased position causes the tap 17 to move downwards in the first part 18a of the slit 18 towards the transverse second part 18b, and the tap 23 of the first insertion part 15 to move up in the slit 24 in a direction parallel to the longitudinal axis of the first insertion part 15. Thus, the elastic element 21 retracts the second insertion part 16 which is fastened to the needle-holding part 19 thereby releasing the injection needle 6 from the cannula device and leaving the cannula 3 within the patient.

In order to reach the state shown in FIG. 29 the pressure is fully released from the second insertion part 16. Here after the second insertion part 16 is rotated to the left causing the tap 17 to move into the middle section of the transverse second part 18b of the slit 18. This rotation at the same time causes tap 23 to move into the short part of the L-shaped slit 24 which is essentially perpendicular to the longitudinal direction, thereby locking both the first insertion part 15 to the second insertion part 16 and locking the needle-holding part 9 within the first insertion part 15. The insertion device can then be safely removed from the receiving portion 7, while the injection needle 6 is kept protected inside the first insertion part 15 and not visible to the patient.

Figure 30:
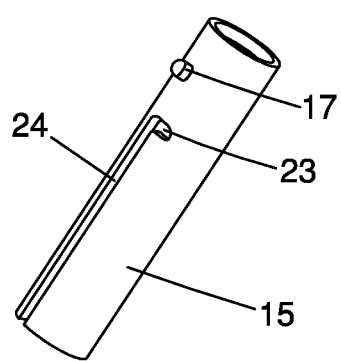
FIG. 30 is a side view of the disposable part of the two-unit, multiple-use insertion device after use, particularly illustrating the disposable part as disconnected from the reusable part and ready for disposal.

FIG. 30 shows the first insertion part 1 after having been removed from the second insertion part 16 after use. The first insertion part 15 containing the used and safely hidden injection needle 6 has been released from the second insertion part 16 and is ready for disposal. The needle-holding part 19 is locked to the inside of the first insertion part 1 via the tap 23 in the L-shaped slit 24, thereby keeping the used injection needle 6 within the first insertion part 15 for safety reasons, when disposed of.

A cannula device according to the present invention can appropriately be used in relation with treatment of diabetes or in relation with deliverance of other drugs where the cannula device is connected to a reservoir and a pump unit or the cannula device can be a part of a gate way system where syringes can be used to feed one or more different drugs to the patient.

A cannula device according to the present invention can also consist of a sensor or a probe which have to have a part positioned subcutaneously in contact with the blood stream of the patient i.e. in order to meter the glucose content of the patient's blood.

The invention claimed is:

1. A cannula device which can be mounted in a base part, the base part during use is secured to a patient's skin, the cannula device comprising:
   a housing and at least one membrane together defining at least one cavity;
   a cannula mounted in the housing and being in fluid communication with the at least one cavity, the cannula extending from a proximal side of the housing, the cannula being configured to be injected subcutaneously;
   means for attaching the cannula device to the base part, the means for attaching the cannula device to the base part are positioned on the proximal side of the housing of the cannula device.

2. A cannula device according to claim 1 wherein the means for attaching the cannula device to the base part comprise attachment members for cooperating with corresponding means on the base part.

3. A cannula device according to claim 2 wherein the means for attaching the cannula device to the base part comprise pivotable members extending from a proximal surface of the cannula device, the pivotable members configured to temporarily reduce the diameter formed by the edges of the pivotable members in at least one position.

4. A cannula device according to claim 1 wherein the means for attaching the cannula device to the base part comprise an adhesive surface on a proximal surface of the cannula device adhering to a corresponding surface of the base part.

5. A cannula device according to claim 1, wherein the cannula device is placed in an inserter device provided with a covering part covering the full length of the cannula device.

6. A cannula device according to claim 1, wherein the device comprises a body having a substantially smooth outer surface and having an inner cavity, the inner cavity comprising a distal end covered with a wall configured to be penetrated by a needle, a proximal end of the inner cavity having the cannula therein, and an outer proximal surface of the body is provided with means for unreleasably attaching the device to a receiving portion.

7. A cannula device according to claim 6, wherein the substantially smooth outer surface has a round, poly-angular or oval circumference.

8. A cannula device according to claim 6 wherein the wall covering the distal end of the inner cavity can be penetrated by a pointed or blunt needle.

9. A cannula device according to claim 6 wherein the unreleasable attachment between the receiving portion and the cannula device is formed automatically as the cannula device is pushed against the receiving portion.

10. An inserter device for insertion of a cannula device according to claim 1, wherein said inserter device comprises a first insertion part and a second insertion part,
    the first insertion part engages with the second insertion part, and said first insertion part is provided with guiding means interacting with corresponding guiding means of the second insertion part for guiding a slidable movement of the first and second insertion parts in relation to each other, and
    an injection needle connected to the second insertion part, the injection needle is releasably connected to the cannula of the cannua device;
    wherein the first insertion part covers the injection needle in a non-activated position and
    wherein the guiding means of the first and the second insertion part allows the injection needle to project beyond the first insertion part when the insertion device is activated.

11. An inserter device according to claim 10, where the first insertion part covers an open space defined in a base part or the skin of the patient during injection and after injection.

12. An inserter device according to claim 11, wherein the cannula device has a retracted position inside the first insertion part and a forward position wherein the cannula of the cannula device extends beyond an open proximal end of the first insertion part.

13. An inserter device according to claim 11, where the first insertion part is provided with guiding means which means can be combined with means of a base part being secured to the patient to define an insertion point and angle.

14. An inserter device according to claim 11, wherein the cannula device corresponds to an internal opening in a part of the inserter and that the cannula device is provided with means for attaching the device to the base part on the proximal side of the cannula device.

15. An inserter device according to claim 10, wherein the inserter is delivered for use as a sterile single-use inserter including a cannula device.

16. An assembly comprising:
    a cannula device provided with a cannula, the cannula extending from a proximal side of the housing and the cannula is configured to be injected subcutaneously, the cannula device comprising attachment members on the proximal side of the cannula device;
    a base part, the base part comprising a receiving portion for the cannula device and an underlying mounting pad,
        the cannula device is positionable in the receiving portion, the cannula device including a housing defining an inner cavity having one or two access openings adapted to receive a piercing member, each access opening of the cannula device is covered with a membrane and a connector needle forms a fluid connection between the reservoir and the cannula device when the reservoir is connected to the cannula device by penetrating a membrane of the cannula device, and
    a delivery part, the delivery part comprising a cover, a reservoir and means for transporting the content of the reservoir to the patient.

17. Assembly according to claim 16, wherein the cannula device is positioned in a sterile single-use inserter before the cannula of the cannula device is inserted subcutaneously in a patient.

18. Assembly according to claim 16, wherein a sterile part comprising an injection needle combined with a cannula device is positioned in a multiple-use inserter before the cannula of the cannula device is inserted subcutaneously in a patient.

19. Assembly according to claim 16, wherein the cannula device is not inserted perpendicular to the patient's skin.

20. Assembly according to claim 19, wherein the cannula device is inserted in an angle of approximately 30°.

21. Assembly according to claim 16, wherein the cannula device has two access openings.

22. Mounting pad comprising a base part provided with a receiving portion for a cannula device and means for positioning an insertion device, the base part comprising attachment parts corresponding to attachments parts on a delivery part, the delivery part comprising a reservoir unit and means for transporting the content of the reservoir to the patient.

23. Mounting pad according to claim 22, wherein an insertion device is positioned before it is activated.

24. Mounting pad according to claim 22, wherein a cannula can be injected subcutaneously after having secured the mounting pad to the skin.

* * * * *